United States Patent [19]

Beck et al.

[11] 4,336,811

[45] Jun. 29, 1982

[54] PROSTHESIS ELECTRODE WITH MULTI-LAYER MEMBRANE

[75] Inventors: Theodore R. Beck, Seattle; Robert T. Ruggeri, Kirkland, both of Wash.

[73] Assignee: Electrochemical Technology Corp., Seattle, Wash.

[21] Appl. No.: 167,201

[22] Filed: Jul. 9, 1980

Related U.S. Application Data

[63] Continuation-in-part of Ser. No. 13,915, Feb. 22, 1979, abandoned.

[51] Int. Cl.³ ............................................. A61N 1/04
[52] U.S. Cl. .................................................... 128/784
[58] Field of Search ............................ 128/783–786, 128/798, 802, 803, 639–642, 644

[56] References Cited

U.S. PATENT DOCUMENTS

| | | | |
|---|---|---|---|
| 3,572,323 | 3/1971 | Yuan | 128/2.06 |
| 3,993,048 | 11/1976 | Francis | 128/2.06 E |
| 3,994,302 | 11/1976 | Brennen | 128/404 |
| 4,011,861 | 3/1977 | Enger | 129/2.06 E |

FOREIGN PATENT DOCUMENTS 9727 4/1980 European Pat. Off. ............ 128/784

*Primary Examiner*—Lee S. Cohen
*Attorney, Agent, or Firm*—Merriam, Marshall & Bicknell

[57] ABSTRACT

A prosthesis electrode for electrically stimulating body tissue. The electrode has a metal tip covered by a non-metallic coating composed of a compound of the metal in the tip. Covering the non-metallic coating is an ion-conducting membrane which prevents the metal tip and the non-metallic coating from contacting the body tissue. The membrane comprises a specific ion-conducting inner membrane layer which prevents transference to the body tissue of ions in the coating which enter into undesirable reactions with the body tissue. On the outside of the inner membrane is a non-specific ion-conducting outer membrane layer which is non-toxic to body tissue and which prevents changes in salt concentration in the body tissue adjacent the electrode during a biphasic pulse of the electrode.

18 Claims, 5 Drawing Figures

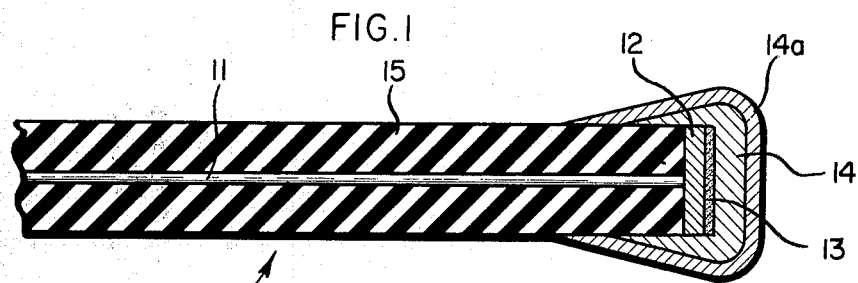
FIG. 1
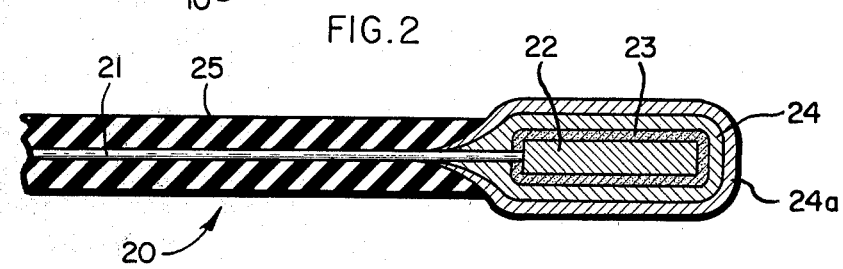
FIG. 2
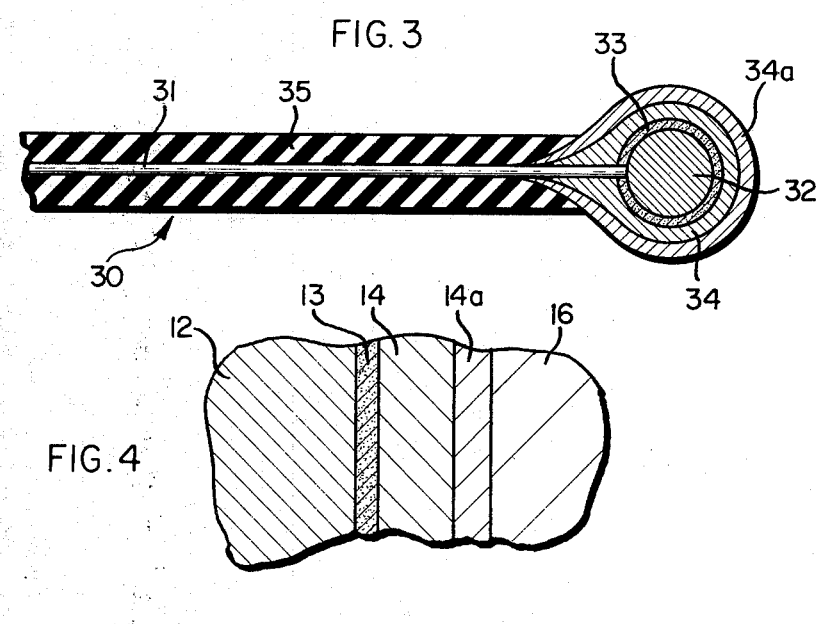
FIG. 3
FIG. 4
FIG. 5

PROSTHESIS ELECTRODE WITH MULTI-LAYER MEMBRANE

RELATED APPLICATION

This is a continuation in part of application Ser. No. 13,915, filed Feb. 22, 1979, now abandoned, and entitled "Prosthesis Electrode", and the subject matter thereof is incorporated herein by reference.

BACKGROUND OF THE INVENTION

The present invention relates generally to electrodes and more particularly to prosthesis electrodes for stimulating nerve tissue or muscular tissue in a body.

For therapeutic purposes it is sometimes desirable to electrically stimulate or excite body tissue. This is done with an electrode implanted in the body next to the body tissue which is to be excited. Problems arise from this practice.

The more conventional electrode was typically composed of metal, such as platinum or tantalum, and the electrical charge is carried by electrons in the metal and by ions in the fluids of the body tissue. When direct current is passed through the electrode to excite the body tissue, there is an electrochemical reaction at the interface between the metal electrode and the body tissue, resulting in degradation or corrosion of the electrode and in the generation of reaction products in the body tissue. These reaction products may be toxic, especially if allowed to build up or accumulate in the body tissue.

In an attempt to avoid the undesirable results arising from the use of direct current, use has been made of biphased, balanced electric waveforms. These comprise alternating positive and negative pulses which result in no direct current over a full cycle and a zero net charge transfer. This approach theoretically reduces electrochemical damage by reversing, in the second part of the waveform, some of the electrochemical reactions occurring during the first part. However, even under these conditions, harmful amounts of reaction products may still accumulate over a period of time, and it is, therefore, desirable that electrochemical reactions at the electrode-tissue interface be avoided altogether. This can be done by limiting the charge passed on a single pulse to that required to charge the so-called electrical double layer, a charge below that which would cause electrochemical reactions. The latter occur when the charge exceeds the breakdown voltage for the capacitance inherently formed between the metal electrode and the body tissue fluid (a natural electrolyte).

Prosthesis electrodes are relatively small, and the amount of charge which can be transferred without electrochemical reaction is proportional to the surface area of the electrode. Accordingly, the surface area imposes limitations on the amount of charge which can be stored. There have been efforts to increase the effective surface area of the all-metal electrode by roughening it, e.g. by peening, etching or platinizing (depositing, by electroplating, a layer of small platinum particles).

Another approach to avoiding the undesirable results arising from the use of all-metal electrodes was the use of capacitor electrodes in which the metal was coated with a thin layer of dielectric material, such as an organic polymer, thereby completely insulating the metal from the body tissue. A biphased, balanced waveform is applied to this electrode.

In general, the capacitance of such electrodes is too small to be practical. This is because the charge must be sufficiently high to excite or stimulate the body tissue. However, if, in order to achieve the stimulus charge, the breakdown voltage of the capacitor is exceeded, there will be a flow of current from the electrode to the body tissue producing the undesired electrochemical reactions.

One form of prior art prothesis electrode of the capacitor type is composed of tantalum coated with a thin layer of tantalum pentoxide as the dielectric material. However, the latter is a good insulator for tantalum for only one polarity of the applied voltage. Therefore, the stimulating electrode would always have to be positive with respect to the body tissue to prevent reduction of the tantalum pentoxide coating and generation of hydrogen gas, which is undesirable. In addition, the amount of charge provided by this type of electrode is too small for many prosthesis applications.

The prosthesis electrode described in the related application provides a high charge transfer capability and long term stability, and it avoids the buildup of toxic reaction products in the body tissue. This prosthesis electrode comprises a metal tip covered by a thin layer of non-metallic coating in turn covered by an ion transfer membrane composed of a single layer of material which is non-toxic to body tissue. The non-metallic coating is preferably composed of a cation corresponding to the metal in the electrode tip and an anion corresponding to an anion in the fluid of the body tissue. Alternatively, the anion in the coating is one which will not form a toxic reaction product when combined with a cation in the body tissue fluid. With either such anion alternative, the membrane is an anion transfer membrane which, during pulsing, inherently permits movement therethrough of the anion in the coating while preventing movement therethrough of the cation in the coating.

In another embodiment of the prosthesis electrode of the related application, the membrane may be a cation transfer membrane, and, in such a case, the cation in the non-metallic coating (and the metal of which the electrode tip is composed) is a cation which, when combined with an anion in the body tissue fluid, produces a compound which is non-toxic or will not build up in toxic quantities in the body tissue (e.g. because it is so insoluble in the body tissue fluid).

In both embodiments of the electrode of the related application, positive charge is passed through the electrode by means of an electrochemical reaction, in the coating, of the metal of the tip to form additional coating or to change the valence state of the cation in the coating. The reverse occurs for passage of negative charge. The ion transfer membrane prevents or inhibits movement into the body tissue fluid of soluble ions of the coating which may have toxicity to the body tissue.

As a result, there may be applied to the electrode of the related application whatever charge is necessary to stimulate the body tissue including the high charge necessary to stimulate optical or auditory nerves, and this may be done without concern about exceeding a breakdown voltage of the capacitor electrode; and there is no need for special manufacturing steps to increase the effective surface area of the electrode to accommodate a large charge without exceeding a breakdown voltage.

The prosthesis electrode of the related application has the capability of stimulating body tissue with a charge or current density which may be from 2 to 10 times higher than that of a more conventional platinum or tantalum electrode. However, there is a problem which arises when such high current or charge densities are used, a problem not recognized with the lower current and charge densities provided by the more conventional platinum and tantalum electrodes.

This problem arises from the presence of sodium chloride in body tissue fluid. At the high current and charge densities available with the prosthesis electrode of the related application, the concentration of the sodium chloride in the body tissue adjacent the electrode will change during a biphasic pulse. More specifically, with a positive pulse of current, chloride ions migrate to the electrode and sodium ions migrate away, resulting in a deficiency of sodium chloride in solution in the tissue at the electrode-tissue interface. A negative pulse gives a corresponding increase in concentration of sodium chloride in the tissue at the electrode-tissue interface. Such changes in the concentration of sodium chloride in the body tissue are undesirable.

SUMMARY OF THE INVENTION

A prosthesis electrode in accordance with the present invention, comprises structure which avoids the changes in salt concentration in tissue adjacent the electrode when the latter is operated at high current density and charge densities.

More particularly, the membrane comprises two layers: an inside layer composed of specific ion-conducting material and an outside layer composed of a non-specific ion-conducting material. The changes in salt concentration occur within the outer membrane layer rather than in the body tissue. This is because the non-specific outer membrane layer conducts both chloride ions and sodium ions in approximately equal amounts. The changes in concentration therefore occur within the non-specific membrane rather than in body tissue. A non-specific membrane outer layer having a thickness of 10,000 to 250,000 Angstroms (1 to 25 microns) will essentially reduce the sodium chloride concentration changes to zero in adjacent tissue.

The inner membrane layer inhibits movement into the body tissue of soluble ions of the coating on the electrode's tip which may be toxic to the body tissue. The outer membrane layer is composed of material which is non-toxic to the body tissue.

Other features and advantages are inherent in the structure claimed and disclosed. They include the features and advantages embodied in the electrode of the related application as well as those which will become apparent to those skilled in the art from the following detailed description in conjunction with the accompanying diagrammatic drawings.

BRIEF DESCRIPTION OF THE DRAWINGS

FIG. 1 is a sectional view of one embodiment of a prosthesis electrode in accordance with the present invention;

FIG. 2 is a sectional view, similar to FIG. 1, of another embodiment of a prosthesis electrode in accordance with the present invention;

FIG. 3 is a sectional view of a further embodiment of a prosthesis electrode in accordance with the present invention;

FIG. 4 is an enlarged, fragmentary, sectional view of a portion of the electrode of FIG. 1; and FIG. 5 is an enlarged, fragmentary, schematic diagram illustrating the reactions which occur during operation of the prosthesis electrode.

DETAILED DESCRIPTION

Referring initially to FIG. 1, indicated generally at 10 is an embodiment of a prosthesis electrode constructed in accordance with the present invention. Electrode 10 comprises a thin metallic wire 11 for conducting an electric signal. Wire 11 is enclosed within electrical insulation material 15. Located at the end of wire 11 is a metallic tip 12 in the form of a disc. The front surface of metal disc 12 is covered by a non-metallic coating 13 which is typically an anodized coating. Coating 13 is composed of a compound of the metal in the tip (e.g. a salt or oxide of the metal). Surrounding the tip is an ion-conducting membrane 14–14a which prevents metal tip 12 and non-metallic coating 13 from contacting body tissue and prevents an electrochemical reaction between the body tissue and the metal tip when the electrode is implanted adjacent the body tissue.

The ion-conducting membrane comprises a specific ion-conducting inner membrane layer 14 adjacent coating 13 and comprising means for inhibiting movement into the body tissue of soluble ions of the coating which may be toxic to the body tissue. The ion-conducting membrane also comprises a non-specific ion-conducting outer membrane layer 14a on the outside of inner layer 14 and comprising means for preventing changes in salt concentration in the body tissue adjacent electrode 10 during a biphasic pulse. Outer membrane layer 14a is composed of a material which is non-toxic to the body tissue.

As noted above electrical insulation 15 encloses wire 11. Metallic tip 12 and non-metallic coating 13 are not enclosed by electrical insulation 15, and the electrode is devoid of electrical insulation at the location where membrane 14–14a overlies non-metallic coating 13.

In the embodiment of prothesis electrode illustrated in FIG. 2, the electrode 20 comprises a thin wire 21 surrounded by electrical insulation 25 and terminating at a metal tip 22 in the form of a cylinder enclosed within a layer of non-metallic coating 23 in turn surrounded by an ion-conducting membrane 24–24a.

In the embodiment illustrated in FIG. 3, the prosthesis electrode 30 has a thin wire 31 enclosed within electrical insulation 35. Wire 31 terminates at a metal tip 32 in the form of a sphere, and metal tip 32 is enclosed within a layer of non-metallic coating 33 in turn surrounded by an ion-conducting membrane 34–34a.

In the embodiments of FIGS. 2 and 3, the ion-conducting membranes are composed of two layers, an inner layer 24 or 34 and an outer layer 24a or 34a. These inner and outer layers correspond to layers 14 and 14a in the embodiment of FIG. 1, and the properties and functions of the layers in FIG. 1 are equally present in the corresponding layers in FIGS. 2 and 3.

As illustrated in FIG. 4, when the electrode is implanted adjacent body tissue 16, the ion-conducting membrane 14–14a is interposed between body tissue 16, on one side, and metal tip 12 and non-metallic coating 13 on the other side, thereby preventing tip 12 and coating 13 from contacting body tissue 16 and for preventing an electrochemical reaction between body tissue 16 and metal tip 12.

In practice, when the prosthesis electrode is implanted adjacent the body tissue, the wire (e.g. 11 in FIG. 1) is connected to one side of a signal generator, and the circuit is completed by another electrode, which may be implanted in the body tissue near the first electrode, and which is connected to the other side of the signal generator. The signal generator alternately generates positive and negative electrical pulses.

In a preferred embodiment, the ion transfer membrane comprises an anion-conducting inner membrane layer 14, and the non-metallic coating 13 comprises an anion corresponding to an anion in the body tissue fluid and a cation corresponding to the metal in the tip. Thus, assuming, for example, that metal tip 12 is composed of silver (the most preferred embodiment), in such a case metal coating 13 would be composed of silver chloride, for example. The chloride ion is an ion corresponding to an ion in the body tissue fluid, namely the chloride ion in sodium chloride, an ingredient occurring in substantial quantities in body tissue fluid. The operation of a prosthesis electrode composed of these materials is illustrated diagramatically in FIG. 5 which depicts the electrochemical reactions, and the ionic transport through the membrane to the surrounding tissue, which occur during alternating positive and negative pulses.

More specifically, on a positive pulse, the following reaction occurs at the interface 17 between silver tip 12 and silver chloride coating 13:

The silver ions (Ag+) migrate through silver chloride layer 13 to the interface 18 between silver chloride layer 13 and inner membrane layer 14. At interface 18 the silver ions react with chloride ions (Cl−) to form more silver chloride film. At the same time, chloride ions are transported from the interface 19 between inner membrane layer 14 and outer membrane layer 14a to interface 18 between inner membrane layer 14 and silver chloride coating 13, where the chloride ions combine with silver ions migrating through silver chloride layer 13. Chloride ions are also transported from the interface 19a, between body tissue 16 and outer membrane layer 14a, to interface 19 and into inner membrane layer 14. Outer membrane layer 14a is conductive to both anions and cations, and the cations (e.g. sodium (Na+) ions) in outer layer 14 are transported from interface 19 to interface 19a, on a positive pulse.

Within body tissue 16, both anions and cations carry the charge. Sodium (Na+) and chloride ions are indicated, for illustration purposes, as they have the highest concentration in body tissue fluid. The chloride ions migrate from body tissue 16 into outer membrane layer 14a, and the sodium ions migrate into surrounding tissue at interface 19a, on a positive pulse.

During a positive pulse, there is no decrease in the concentration of sodium chloride in the body tissue adjacent the electrode at interface 19a because sodium ions are transported to interface 19a from outer membrane layer 14a and chloride ions are transported to interface 19a from body tissue 16, and the sodium and chloride ions thus transported can combine at interface 19a to make up any deficiency in sodium chloride which might otherwise occur there due to the transport from interface 19a of chloride ions into outer layer 14a and sodium ions into surrounding body tissue 16.

To the extent that there is a decrease anywhere in sodium chloride concentration during a positive pulse, it occurs in outer membrane layer 14a from which there is transported sodium ions to interface 19a and chloride ions to interface 19. Absent non-specific ion-conducting outer layer 14a, the decrease in sodium chloride concentration during a positive pulse would occur in body tissue 16, and that would be undesirable.

On a negative pulse, the reactions and the ionic transport directions described above in connection with a positive pulse, are reversed (see FIG. 5).

During a negative pulse, there is no increase in the concentration of sodium chloride in the body tissue adjacent the electrode at interface 19a because sodium ions are transported away from interface 19a into outer membrane layer 14a and chloride ions are transported away from interface 19a into body tissue 16, and the sodium and chloride ions thus transported from interface 19a offset any build-up there of sodium chloride which might otherwise occur due to the transport to interface 19a of chloride ions from outer layer 14a and sodium ions from surrounding body tissue 16.

To the extent that there is an increase anywhere in sodium chloride concentration during a negative pulse, it occurs in outer membrane layer 14a into which there is transported sodium ions from interface 19a and chloride ions from interface 19. Absent non-specific ion-conducting outer layer 14a, the increase in sodium chloride concentration during a negative pulse would occur in body tissue 16, and that would be undesirable.

Accordingly, over a complete cycle, consisting of equal positive and negative pulses, the system returns to the starting condition, the AgCl compound having undergone oxidation and reduction in response to the biphasic pulse, and there is no change in sodium chloride concentration in the body tissue adjacent the electrode.

During a positive pulse, the reaction of silver ions and chloride ions at interface 18 results in the build-up on coating 13 of additional molecular layers of silver chloride, thereby to increase the charge at the tip of the electrode.

As indicated above, the metal tip is preferably composed of silver. When the metal tip is disc-shaped as at 12 in FIG. 1, it typically has a diameter of about 1 millimeter. The thickness of metal disc 12 may be like that of metal foil, and, if the metal foil is not sufficiently rigid, the metal disc may be backed up by a rigidifying element composed of a non-conductive, physiologically inert material. Such materials include, for example, polyethylene or epoxy resins.

When the metal tip is in the form of a sphere, as at 32 in FIG. 3, the sphere may also have a diameter of about one millimeter. When the metal tip is in the form of a cylinder, as at 22 in FIG. 2, it may have a diameter of abut 0.001 inch (0.025 millimeters).

A non-metallic coating on the metal tip typically has an initial thickness in the range 0 to 100,000 molecular layers, and this is so for all of the embodiments of the non-metallic coating (13, 23 and 33). When the initial thickness is zero, molecular layers of the coating accumulate during the positive part of the biphasic pulse and then dissipate to zero thickness during the negative part of the pulse. In such a situation, the positive part of the pulse must come first when the current is turned on.

The ion-conducting membrane generally has a thickness between 1 micron and 100 microns, and this is so for all the embodiments of the ion-conducting membrane (14, 24 and 34).

As indicated above, when the metal tip is composed of silver, the non-metallic coating is preferably composed of silver chloride. However, in all embodiments in which the specific ion-conducting inner membrane layer is anion-conducting, the non-metallic coating should include an anion which corresponds to an anion in the body tissue fluid or which is non-toxic when combined with a cation in the body tissue fluid.

Another metal which may be employed in the metal tip when the membrane is anion-conducting, is mercury, in which case the non-metallic coating for the electrode would be mercury chloride.

When the specific ion-conducting inner membrane layer is cation-conducting, the requirements described in the next to last paragraph need not be imposed upon the anion part of the non-metallic coating; however, additional requirements must be imposed upon the cation in the non-metallic coating. In such a case, the cation must be one which, when combined with an anion in the body tissue fluid, forms a compound which is not toxic or which does not build up in amounts which are toxic to the body tissue.

Thus, assuming a cation-conducting inner membrane layer, the cation in the non-metallic coating should correspond to the metal in the metal tip (e.g. silver). If the cation is silver, and the inner membrane layer is cation-conducting, some silver ion will migrate through the inner and outer membrane layers into the body tissue. The amount of silver so migrating will be very limited, however, because the solubility of the silver ion is very small in body tissue fluid which normally contains approximately 0.1 molar sodium chloride. Under these conditions, the solubility of the silver ion in body tissue fluid would be no greater than one-tenth part per billion, by weight (ppb.) Therefore, even with a cation-conducting inner membrane layer, most of the current is carried by the sodium ion, and little silver ion migrates into the body tissue, particularly if, for a biphasic pulse, the negative pulse is first. Another metal which may be employed in the metal tip of the electrode when the inner membrane layer is cation-conducting, is tungsten (W). In such an electrode, the non-metallic coating would be composed of tungsten oxides ($WO_2$ and $W_2O_5$).

In that electrode, on a positive pulse, the following reaction occurs in the non-metallic coating:

$$2WO_2 + H_2O \rightarrow W_2O_5 + 2H^+ + 2e^-$$

The $H_2O$ in this reaction was absorbed into the coating from the body tissue fluid, or it may have been in the coating before the electrode was implanted in the body tissue. The $H^+$ cations from the reaction do not migrate through the cation-conducting inner membrane layer. Only $Na^+$ cations migrate through the inner membrane layer, in the direction of the body tissue fluid (from whence the $Na^+$ cations originated). There is no migration of $H^+$ cations because the pulses are of such short duration (typically 10-400 cycles per second) that the $H^+$ cations never move very far away from the coating/membrane interface, and there is merely a fluctuation in the concentration of $H^+$ cations adjacent that interface. The tungsten does not ionize into $W^+$ cations, but forms $WO_4^=$ anions at the metal/coating interface. Being anions, the $WO_4^=$ won't move through the membrane because the latter is cation-conducting.

In the body tissue fluid, during a positive pulse, $Na^+$ cations migrate away from, and $Cl^-$ anions migrate toward, the membrane/body tissue interface. $Cl^-$ anions won't move through the inner membrane layer which is cation-conducting.

On a negative pulse, the reactions described above for the positive pulse, are reversed, as are the directions of migration for the various ions.

Examples of anion-conducting membrane materials are organic polymers containing amine groups, either secondary, tertiary or quaternary, such as cross-linked styrene:

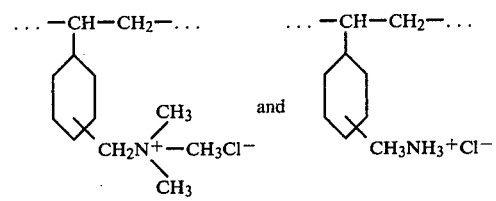

Examples of cation-conducting membrane materials are cross-linked polystyrene with sulfonic acid groups:

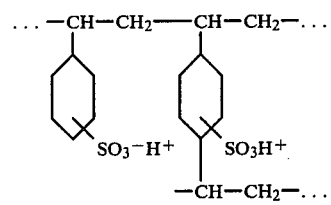

An anion-conducting membrane is a membrane which has a high anion transference number. A perfect anion transference number is 1.0. A high anion transference number, in the context of the present invention, is in the range 0.6 to 1.0. A membrane with a high anion transference number permits the migration therethrough of anions but prevents the migration therethrough of cations. Similarly, a membrane with a high cation transference number has just the opposite effect.

As noted above, the inner membrane layer (e.g. 14) is composed of a specific ion-conducting material which may be either anion-conducting or cation-conducting.

A membrane layer with an ion transference number of 0.5 is equally conductive to anions and cations and is thus a non-specific ion-conducting material. An example of such a material is cellulose acetate which may be used as the outer membrane layer (e.g. 14a). Another material which may be used as the outer membrane layer is a polymer having the following formula:

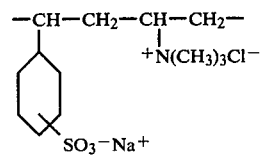

Other examples of ion-conducting materials are described in Kirk-Othmer, Encyclopedia of Chemical Technology, 2d. Edition, Vol. 11, pp. 874–877, and the description therein is incorporated herein by reference.

The foregoing detailed description has been given for clearness of understanding only, and no unnecessary limitations should be understood therefrom, as modifications will be obvious to those skilled in the art.

What is claimed is:

1. A prosthesis electrode for electrically stimulating body tissue, said electrode comprising:
   wire means for conducting an electric signal;
   a metallic tip at the end of said wire means;
   a non-metallic coating on said tip, said non-metallic coating being composed of a compound which can be oxidized and reduced cyclically in response to a biphasic pulse;
   ion-conducting membrane means surrounding said tip and overlying said non-metallic coating for preventing the tip and said coating from contacting said body tissue;
   said coating being in the form of a layer interposed between said tip and said membrane means;
   said membrane means comprising a specific ion-conducting inner membrane layer adjacent said coating and comprising means for inhibiting movement into said body tissue of soluble ions of said coating which may be toxic to the body tissue;
   said membrane means also comprising a non-specific ion-conducting outer membrane layer on the side of said inner membrane layer opposite said coating, said outer membrane layer comprising means for preventing changes in salt concentration in the body tissue adjacent said electrode during a biphasic pulse;
   said outer membrane layer being composed of a material which is non-toxic to said body tissue.

2. A prosthesis electrode as recited in claim 1 and comprising:
   electrical insulation means enclosing said wire means;
   said metallic tip and said non-metallic coating on said tip being substantially exposed relative to said electrical insulation means;
   said electrode being devoid of electrical insulation means at the location where said membrane means overlies said non-metallic coating.

3. A prosthesis electrode as recited in claim 1 wherein:
   said non-metallic coating is a chloride salt of the metal in said tip;
   said inner membrane layer is composed of an anionic-conducting material;
   and said outer membrane layer comprises means for preventing changes in the sodium chloride concentration in said body tissue adjacent said electrode.

4. A prosthesis electrode as recited in claim 3 wherein:
   said non-metallic coating is composed of silver chloride;
   and said metallic tip is composed of silver.

5. A prosthesis electrode as recited in claim 1 wherein:
   said outer membrane layer is composed of cellulose acetate.

6. A prosthesis electrode as recited in claim 1 wherein:
   said inner membrane layer comprises an anion-conducting membrane.

7. A prosthesis electrode as recited in claim 6 wherein:
   said non-metallic coating comprises an anion corresponding to an anion in the body tissue fluid.

8. A prosthesis electrode as recited in claim 7 wherein:
   said non-metallic coating comprises a cation corresponding to the metal in said tip.

9. A prosthesis electrode as recited in claim 8 wherein:
   said metal tip is mercury and said coating is mercury chloride.

10. A prosthesis electrode as recited in claim 1 wherein:
    said electrode is intended for use with a signal generator alternately generating positive and negative electrical pulses, and wherein:
    said non-metallic coating comprises a cation corresponding to the metal in said tip and an anion corresponding to an anion in the body tissue fluid;
    said electrode comprising means for cooperating with said body tissue fluid, and responsive to a positive electrical pulse, for building up on said non-metallic coating additional molecular layers of said coating to increase the charge at the tip of said electrode.

11. A prosthesis electrode as recited in claim 1 wherein:
    said membrane means comprises cation-conducting means;
    and said non-metallic coating comprises a cation which is substantially insoluble in the body tissue fluid.

12. A prosthesis electrode as recited in claim 11 wherein:
    said non-metallic coating comprises a cation having a solubility in said body tissue fluid no greater than 0.1 ppb.

13. A prosthesis electrode as recited in claim 1 wherein:
    said inner membrane layer comprises cation-conducting means.

14. A prosthesis electrode as recited in claim 13 wherein:
    said metallic tip is composed of tungsten;
    and said coating comprises oxides of tungsten.

15. A prosthesis electrode as recited in claim 13 wherein:
    said metallic tip is composed of silver.

16. A prosthesis electrode as recited in claim 1 wherein:
    said non-metallic coating has an initial thickness in the range 0–100,000 molecular layers.

17. A prosthesis electrode as recited in claim 1 wherein:
    said membrane means has a thickness in the range 1–100 microns.

18. A prosthesis electrode as recited in claim 17 wherein:
    said non-metallic coating has an initial thickness in the range 0–100,000 molecular layers.

* * * * *